United States Patent [19]

Alers et al.

[11] Patent Number: 4,777,824

[45] Date of Patent: Oct. 18, 1988

[54] ELECTROMAGNETIC ACOUSTIC TRANSDUCER

[75] Inventors: George A. Alers; Leigh R. Burns, Jr., both of Albuquerque; Daniel T. MacLauchlan, Sandia Park, all of N. Mex.

[73] Assignee: Magnasonics, Inc., Albuquerque, N. Mex.

[21] Appl. No.: 66,772

[22] Filed: Jun. 25, 1987

[51] Int. Cl.⁴ ............................................. G01N 29/04
[52] U.S. Cl. ........................................ 73/643; 324/226
[58] Field of Search ................... 324/226; 73/643, 597

[56] References Cited

U.S. PATENT DOCUMENTS

| | | |
|---|---|---|
| 3,460,063 | 8/1969 | Houck . |
| 3,583,213 | 6/1971 | Houck et al. . |
| 3,850,028 | 11/1974 | Thompson et al. . |
| 4,295,214 | 10/1981 | Thompson et al. . |
| 4,466,287 | 8/1984 | Repplinger et al. . |
| 4,578,999 | 4/1986 | Abend et al. ............... 73/643 |
| 4,593,567 | 6/1986 | Isselstein et al. ............ 73/643 |

OTHER PUBLICATIONS

"Generation of Ultrasonic Waves Without Using a Transducer", E. R. Dobbs and J. D. Llewellyn, pp. 49–56 in Non-Destructive Testing, vol. 4, No. 1, Feb. 1971.

*Ultrasonic Transducers for Non Destructive Testing* M. G. Silk, Adam Hilger Ltd, Bristol, U.K. 1984, pp. 111–119.

Legg, K. O., and Meredith, D. J., *Journal of Physics D, Applied Physics*, vol. 3 (1970), pp. L61–L63.

Wallace, W. D., Houck, J. R., Bowers, R., Maxfield, B. W., and Gaerttner, M. R., 1968, *Review of Scientific Instruments*, vol. 39, pp. 1863–1864.

"Pulsed Laser/Electromagnetic Acoustic Transducer Approach to Ultrasonic Sensor Needs for Steel Processing," by G. A. Alers and H. N. G. Wadley, pp. 627–638 in Rev. Prog. in Quantitative Nondestructive Evaluation, vol. 6A, 1987.

*Primary Examiner*—John Chapman
*Assistant Examiner*—Robert P. Bell
*Attorney, Agent, or Firm*—Gregory O. Garmong

[57] ABSTRACT

A noncontact ultrasonic transducer for studying the acoustic properties of a metal workpiece includes a generally planar magnetizing coil positioned above the surface of the workpiece, and a generally planar eddy current coil between the magnetizing coil and the workpiece. When a large current is passed through the magnetizing coil, a large magnetic field is applied to the near-surface regions of the workpiece. The eddy current coil can then be operated as a transmitter by passing an alternating current therethrough to excite ultrasonic waves in the surface of the workpiece, or operated as a passive receiver to sense ultrasonic waves in the surface by measuring the output signal. The geometries of the two coils can be varied widely to be effective for different types of ultrasonic waves. The coils are preferably packaged in a housing which does not interfere with their operation, but protects them from a variety of adverse environmental conditions.

17 Claims, 5 Drawing Sheets

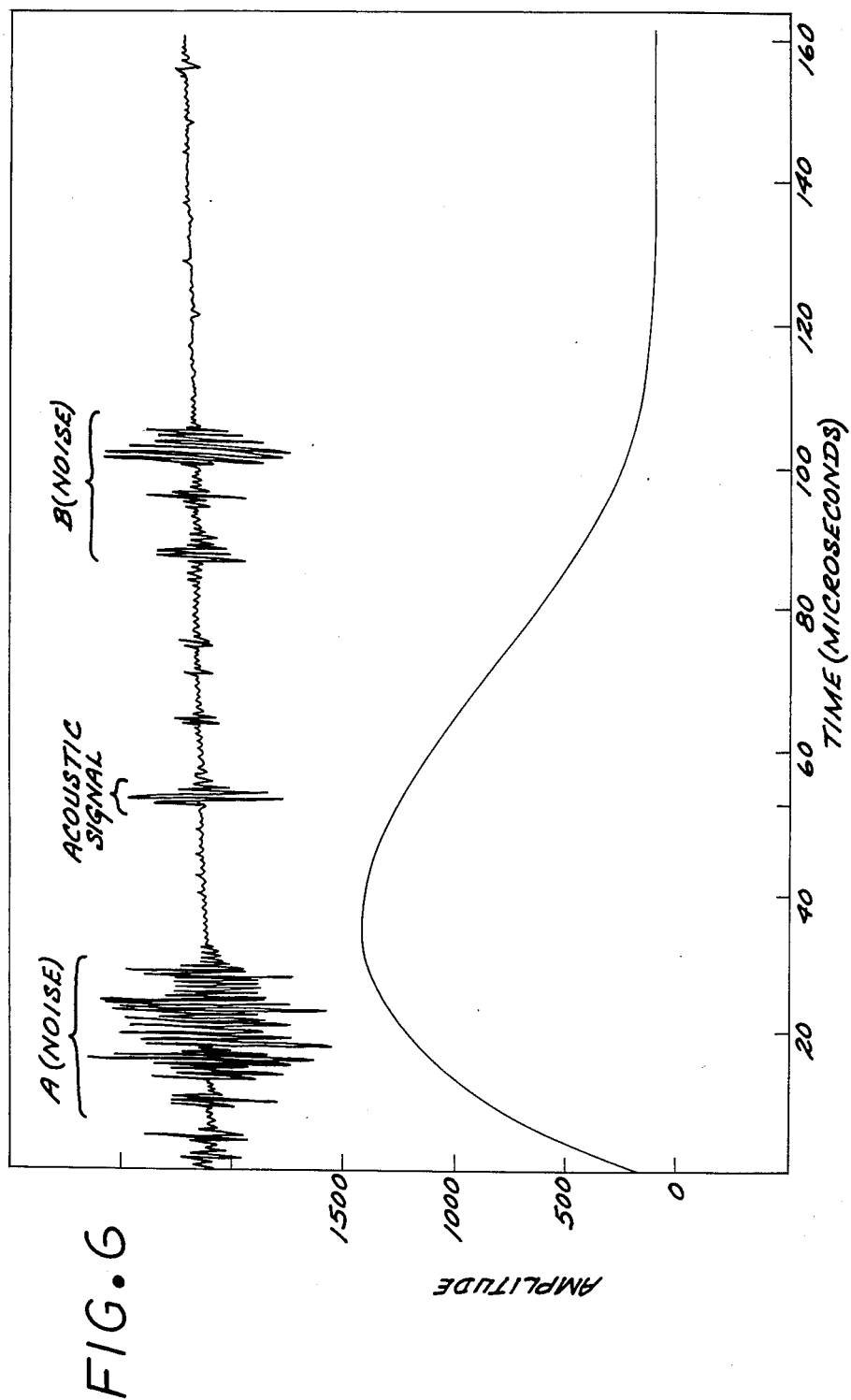

4,777,824

ELECTROMAGNETIC ACOUSTIC TRANSDUCER

BACKGROUND OF THE INVENTION

This invention relates to transducers used to excite and receive acoustic waves in a metal workpiece, and, more particularly, to noncontact transducers that do not require a couplant between the transducer and the workpiece.

A variety of techniques are known for analyzing and characterizing materials and workpieces, and then predicting their subsequent service behavior. For many years, the techniques had been based upon destructive testing, wherein a piece of the material was evaluated by a methodology which then rendered it unfit for further service, such as mechanical testing to failure or metallography. From the destructive test results, predictions are made for the performance of similar parts in service. Of course, the actual service part cannot be evaluated directly, because it is destroyed in the testing procedure. The viability of this type of testing depends upon the ability to predict the performance of one part from tests made on another part, and materials scientists and engineers have long recognized that in many instances such predictive capability is not yet available.

Nondestructive testing, wherein a part or workpiece is evaluated by a procedure that does not damage or destroy it, has become of greater interest as materials are used in ever more demanding applications. The predictive inaccuracies associated with destructive testing become more significant when smaller design margins are available. Nondestructive testing offers a way to evaluate the very workpiece that is to be used in service, thereby avoiding many of the predictive problems in going from the tested piece to the service piece. A number of nondestructive test procedures have been developed, and some are now regularly used. One continuing effort has been to improve nondestructive testing procedures and to broaden the scope of operations that can benefit from the use of such techniques.

One of the most widely used nondestructive test techniques is ultrasonic testing, in which a sound wave, typically of a frequency that is too high to be heard by the human ear, is introduced into a workpiece and then received and evaluated after it has passed through a portion of the piece. Some properties of the workpiece, such as its modulus of elasticity, can be determined directly from the received sound wave, while others require more sophisticated analysis of the wave. Ultrasonic testing is now widely used to predict the remaining life expectancy of a part actually in service, and from these results develop better materials and production methods for extending the operating lives of subsequently produced parts.

A critical part of an ultrasonic testing system is the transducers that produce sound waves in the workpiece, and receive sound waves from the piece. These transducers must be able to function with waves of the desired frequency, under the required environmental conditions. Families of transducers have been developed for such testing. Typically, such transducers are piezoelectric transducers, using a crystal wherein an introduced electric signal produces a mechanical movement of the crystal. The crystal is acoustically contacted to the workpiece, either directly or indirectly with a coupling medium, so that the movement is transmitted into the workpiece, resulting in an acoustic wave. The received wave can similarly be detected with a piezoelectric crystal, with a small mechanical movement of the acoustic wave producing a measurable electric signal. Such transducers are widely and successfully used in many applications.

However, there are other applications where contacting transducers cannot be readily used. For example, if a part is used at high temperatures or pressures, in high levels of radiation, or in other adverse environments, then it is desirable to be able to actually test it at that temperature while in service. Contacting transducers often cannot be used under these conditions, because of the inability to couple the transducer to the workpiece, or because the environment damages the transducer.

There are now available noncontacting ultrasonic transducers. Such transducers permit introduction or reception of sound waves without being physically coupled to the workpiece (although the transducer may lightly touch or rest upon the workpiece without a coupling medium therebetween). The most important type of such transducer is the electromagnetic acoustic transducer, or EMAT. The EMAT includes a large magnet that applies a high intensity magnetic field to the surface of the metallic workpiece, and an electromagnetic excitation or eddy current coil operating above the surface in the magnetic field. It is not necessary that either coil actually touch the workpiece. When a signal is applied to the eddy current coil, a corresponding signal is transmitted into the surface of the workpiece. Similarly, a wave in the surface may be detected with an EMAT placed above the surface.

EMATs have the potential of extensive use in a variety of nondestructive testing applications, but current versions have some important drawbacks. Existing EMATs are bulky and difficult to package as a small, versatile unit. There have been proposed no effective EMAT designs for use in highly adverse environments such as high temperatures. The existing EMATs can produce a variety of types of ultrasonic waves in the workpieces. By contrast, the existing contact-type transducers are much smaller and more convenient to use, but can produce only a limited number of ultrasonic wave types. Finally, the power of existing small EMATs is limited by their design.

Accordingly, there exists a need for an improved electromagnetic acoustic transducer that is compact yet powerful, operable in adverse environments, and versatile. The present invention fulfills this need, and further provides related advantages.

SUMMARY OF THE INVENTION

The present invention provides a noncontacting, couplant free electromagnetic acoustic transducer (EMAT) that induces a strong acoustic wave in a workpiece without contacting the surface of the piece, yet is operable in small sizes. The EMAT can be packaged in a housing that protects it from environmental damage yet does not interfere with its operation. The EMAT of the invention is operable with workpieces in extremely adverse environments, as for example temperatures of 2000° F., high pressures, and high radiation fluxes. A variety of types of acoustic waves can be transmitted into, or received from, the workpiece, permitting many types of testing procedures to be performed.

In accordance with the invention, an electromagnetic acoustic transducer for testing a metallic workpiece comprises a generally planar, electrically conductive magnetization coil, a generally planar, electrically conductive electromagnetic eddy current coil, and means for mounting the eddy current coil between the magnetization coil and the workpiece, but without touching the workpiece. In a packaged form, an electromagnetic acoustic transducer comprises a housing having a base, the housing being constructed of a poorly conducting material, a generally planar, electrically conductive magnetization coil, mounted with its plane parallel to the base, and a generally planar, electrically conductive electromagnetic eddy current coil with its plane parallel to the base disposed between the magnetization coil and the base, the magnetization coil and the electromagnetic eddy current coil being contained within the housing.

The magnetization coil is a coil of electrically conductive wire that can be wound in any of a variety of forms, all of which are generally planar. By "generally planar" is meant that the coil lies in a plane, although there may be minor deviation from perfect planarity, either intentionally or unintentionally. The wire of the magnetization coil typically carries a high current, and the wires are of a thick gage. The turns of wire are therefore insulated from each other by a conventional electrical insulation, or by a specially selected insulation if the transducer is to be operated in environmentally hostile conditions. For example, the insulation can be fiberglass, mica or a ceramic, if necessary. The magnetization coil is therefore generally pancake in shape.

Similarly, the eddy current coil is a coil of electrically conductive wire in any of several forms, all of which are generally planar. The eddy current coil is ordinarily made of a fine gage wire, as the current carried is not large. The eddy current coil is often mounted to a nonconducting substrate for support. Insulation of the individual turns is not required in such cases.

As will be discussed in detail, the magnetization coil and the eddy current coil can be wound in many different forms. Variations in the configurations of the two coils together permit a wide variety of different types of waves to be transmitted into, and received from, the workpiece.

The primary function of the mounting means and housing is to support the two coils relative to each other and to the workpiece under analysis. The magnetization coil is supported close to the surface of the workpiece, with its plane parallel to that of the surface. The eddy current coil is sandwiched between the magnetization coil and the surface, but physically separated from the surface. The theory of such transducers suggests that the efficiency and power of the noncontacting EMAT transducer depends upon placing the two coils as closely as possible to the surface, without actually touching it. The housing is therefore designed so that its base, the portion separating the eddy current coil from the surface of the workpiece, is as thin as possible under the particular circumstances of testing. The housing should also not interfere with the basic functioning of the transducer. It is therefore typically made of a nonconducting or poorly conducting material that does not substantially alter the magnetic flux lines of the magnetization coil or attenuate its signal or have an induced current from the magnetic field. Generally, materials having a resistivity of at least about 50 microohm-centimeter are suitable.

Briefly, the transducer of the invention transmits or induces waves in the workpiece by establishing a strong magnetic field in the surface or upper skin layers of the workpiece, through the field induced by the magnetization coil. The eddy current coil produces an electromagnetic field in the electrically conductive or magnetic workpiece that reacts with the magnetic field to cause a small mechanical displacement at the surface or in the near-surface regions. By driving the eddy current coil with a time varying signal, a corresponding displacement wave is induced in the workpiece, and this mechanical wave is propagated away from the region of the EMAT.

The transducer may also be operated to receive waves. Small displacements in the surface or near surface region perturb the applied magnetic signal, inducing a corresponding signal in the eddy current coil. This electrical signal can then be amplified and studied. A comparison of the transmitted and received waves permits a great deal of information to be deduced about the structure and properties of the workpiece. In some instances, the same transducer is used to transmit and receive the acoustic waves, and in other instances two transducers are used.

The strength of the acoustic wave transmitted into the workpiece is important, as high amplitudes permit detection and evaluation of ever finer features of the workpiece. One determinant of the strength of the wave in the workpiece is the proximity of the coils to the workpiece, without touching the workpiece, as previously discussed. Another determinant is the strength of the magnetic field induced by the magnetization coil. The stronger the magnetic field, the greater the amplitude of the acoustic wave. In prior EMATs, a high magnetic field, typically on the order of about 1 Tesla, was achieved using a large, bulky electromagnet or possibly a permanent magnet.

To achieve a strong magnetic field in the apparatus of the present invention, the electromagnet in the form of the magnetization coil is driven by as high a current as possible, and the separation distances between the coils and the workpiece are kept as small as reasonably possible to prevent the magnetic field from being spread over a large volume. A high current is preferably achieved by sending a large pulse of current, on the order of 1000 amperes or greater through the magnetization coil. A magnetic field is thereby applied to the nearby surface of the workpiece, and then the eddy current coil is operated while the magnetic field is present. Typically, the induced acoustic wave radiates outwardly from the region of the magnetic field and the eddy current, and returns before the magnetic field begins to decay. Alternatively, a steady current can be passed through the magnetization coil to produce a steady magnetic field in the workpiece, but this approach suffers from the disadvantages of deeper penetration of the field into the surface and waste of power. At the high current levels used to drive the magnetization coil, electrical power consumption can become a significant consideration in the overall economics of using the transducer.

Thus, in accordance with the invention, a method for performing acoustic wave testing of a workpiece comprises the steps of furnishing an electromagnetic acoustic transducer, comprising a housing having a base, the housing being constructed of a poorly conducting material, a generally planar, electrically conductive magnetization coil, mounted with its plane parallel to the base, and a generally planar, electrically conductive eddy current coil with its plane parallel to the base, and disposed between the magnetization coil and the base, the magnetization coil and the eddy current coil being contained within the housing; positioning the base adjacent and parallel to the workpiece to be measured; and measuring the propagation of acoustic waves in the workpiece using the electromagnetic acoustic transducer. In the measuring step, the EMAT can be used for either transmitting the acoustic wave, when the eddy current coil is driven, or for receiving the acoustic wave, when the eddy current coil is excited by the wave and the resulting signal induced in the coil amplified and detected.

As is apparent, the EMAT of the invention may be used in conjunction with other apparatus for the measurement of acoustic waves in solids. The EMAT of the invention may be used to excite acoustic waves in the solid, and the resulting waves received by another device. The acoustic waves may be excited using another means, and the EMAT of the invention used only to receive the propagated waves. In this latter connection, some current practice utilizes a laser to excite a longitudinal compression acoustic wave in a workpiece. The EMAT of the invention can be used to receive the wave so produced. However, it is preferred to use the EMAT to excite the acoustic waves as well as detect them, as many more different modes of wave propagation may be transmitted with the EMAT than with prior devices such as lasers, with the result that far more information may be determined about the workpiece.

Some existing EMATs utilize a pulsed iron core electromagnet to achieve high magnetic fields in a workpiece. The present invention, utilizing a generally planar magnetization coil, requires no core for the electromagnet. Avoiding the use of a core has important benefits. The duration of the current pulses can be shortened sustantially where no core is present, because of the smaller inductance, leading to lower power consumption and cooling requirements. When a ferromagnetic material such as most steels is the workpiece, the reduction in the duration of the pulse causes the magnetic field to be concentrated in a very thin layer of the surface of the workpiece, so that exceptionally high magnetic fields are developed for currents of moderate size. The conventional electromagnet with a ferromagnetic core applies a large magnetic induction field in a direction perpendicular to the workpiece surface, emanating from a pole piece. This unneeded induction field is eliminated in the present invention, and the magnetization coil applies a tangential magnetic field directly to the surface of the workpiece through the combination of a high pulse current and a small working distance between the coils and the workpiece.

The elimination of the core also reduces the size and weight of the electromagnet, an important benefit for commercial applications. Typical conventional EMATs having an iron core electromagnet weigh on the order of about 100 pounds, and may be 6-8 inches on a side in a package. The EMAT of the present invention having equal or superior performance may weigh only about 1 pound, and fit within a package that is only 2 inches or smaller in size.

It will now be apparent that the electromagnetic acoustic transducer of the invention presents a significant advance in the art of noncontacting acoustic transducers. The transducer of the invention may be made compact yet powerful, and may be made to operate in adverse environments that render conventional transducers inoperable. The EMAT also can produce a wide range of acoustic waves, by selecting specific configurations for the magnetization coil and the eddy current coil. Other features and advantages of the invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 6 is a tracing of an oscilloscope display of an ultrasonic waveform received by an EMAT receiver from a laser-induced acoustic wave.

DETAILED DESCRIPTION OF THE PREFERRED EMBODIMENT

Figure 1:
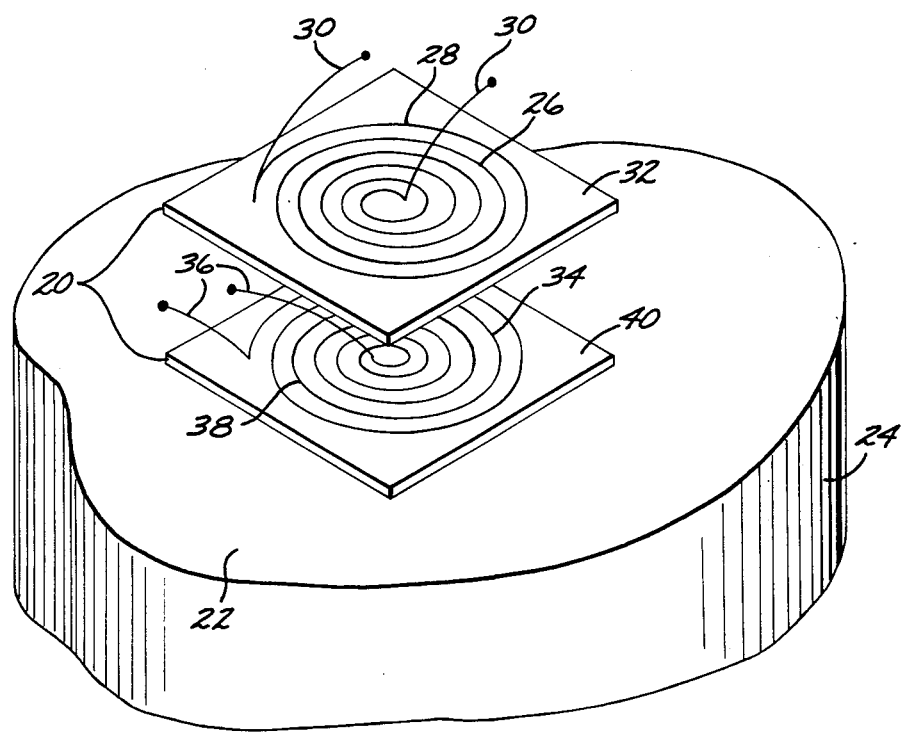
FIG. 1 is a perspective view of an EMAT.

As illustrated in FIG. 1, an electromagnetic acoustic transducer (or EMAT) 20 is positioned above a surface 22 of a workpiece 24. The EMAT 20 includes a generally planar magnetization coil 26, formed by a length of wire 28 wound or bent into a shape that is substantially planar. The wire is a conducting material having low electrical resistance, such as copper. Two leads 30 extend from the coil 26. Since in use a large electrical current is passed through the coil 26, the turns of the coil 26 must be prevented from touching each other. This may be done by supporting the coil 26 on an insulator support 32 in a manner such that the turns of wire do not touch and the coil 26 remains planar, as illustrated in FIG. 1. Alternatively, the turns of wire can be individually insulated by an appropriate insulator material. For example, if the EMAT 20 is to be used at elevated temperature, the insulation must be selected to withstand that temperature. Such high temperature insulation includes fiberglass or ceramic.

The EMAT 20 further includes a generally planar eddy current coil 34, having leads 36 extending therefrom. (The eddy current coil is also sometimes termed an EMAT coil.) As in the case of the magnetization coil 26, the wire 38 making up the eddy current coil 34 is wound or bent into a shape that is substantially planar. The turns of wire 38 should be insulated from each other, as by mounting the coil 34 on an insulator support 40, which also serves to maintain the planar character of the coil 34. Other insulating techniques, as appropriate, may be used.

The magnetization coil 26 and the eddy current coil 34 are mounted so that their planes are substantially parallel to each other within the EMAT 20. In use, the plane of the magnetization coil 26 and the eddy current coil 34 is parallel to the plane of the surface 22 of the workpiece 24. Minor misorientations of a few degrees between the various planes are tolerated, but larger misorientations can have a significant adverse effect in reducing the efficiency of the EMAT 20 or altering the waveform of the acoustic wave.

Figure 2:
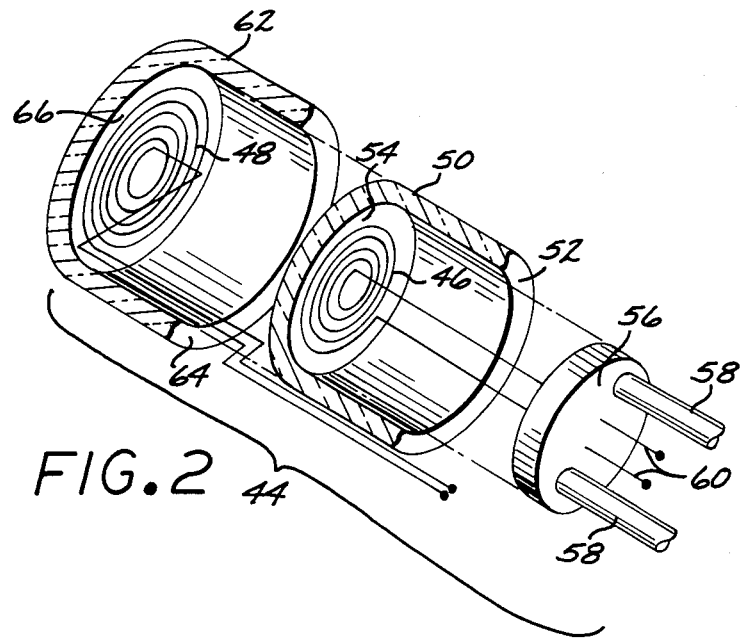
FIG. 2 is an exploded perspective view, with portions broken away, of a packaged EMAT.

Another embodiment of the EMAT is illustrated in FIG. 2, in a packaged form suitable for testing and measuring acoustic wave propagation at elevated temperature. It will be appreciated that the general form of EMAT illustrated in FIG. 1 can be used in a few laboratory or undemanding operational environments, but that further packaging of the components within a housing is necessary for most applications to prevent damage to the components and easy use by operators.

A high temperature EMAT 44 includes a generally planar magnetization coil 46 and a generally planar eddy current coil 48. The magnetization coil 46 is supported in a container 50 having a cylindrical outer wall 52 and a flat, circular interior support surface 54 whose normal is parallel to the axis of the cylinder. The magnetization coil 46, having turns that are individually insulated from each other with fiberglass or a ceramic, rests on the support surface 54. The container 50 is constructed of a material that is heat resistant and non-magnetic, but a conductor of heat. Type 410 stainless steel, titanium, or a ceramic such as alumina is presently preferred for construction of the container 50. The coil 48 is fabricated from wire having a melting point well above the intended temperature of use.

A circular cap 56 is joined to one end of the container 50 in a water-tight fashion. Water cooling to the interior of the container 50 is provided by two bores through the cap 56, with two tubes 58 as inlet and outlet for water. The interior of the container 50, and the magnetization coil 46, are cooled by the water. Electrical feedthroughs 60 are provided to pass the leads to the coil 46 through the cap 56.

The eddy current coil 48 is supported within a cup 62, which, together with the container 50, constitutes a housing for the EMAT 44. The cup 62 includes a cylindrical outer wall 64 and a base 66. The inner diameter of the outer wall 64 is dimensioned to be slightly larger than the outer diameter of the wall 52, so that the cup 62 slidably engages over the container 50. The two pieces 62 and 50 can be semi-permanently or permanently joined together at the open end of the cup 62, as by gluing with a high temperature adhesive. The base 66 is thus the bottom of the cup 62. The eddy current coil 48 preferably rests on the interior surface of the base 66. The base is made as thin as is reasonably possible, so that the eddy current coil 48 and the magnetization coil 46 are positioned as closely as possible to the surface of a workpiece. The base 66 may be made with a thickness less than about 0.005 inches, and the distance from the magnetization coil 46 to the outer surface of the base 66 may be made to be less than about 0.010 inches. In operation, the outer surface of the base 66 is placed closely adjacent the surface of the workpiece being measured. The cup 62 is typically made of a ceramic such as alumina, and the wire of the eddy current coil 48 is made of a material having a sufficiently high melting point to resist damage at the temperature of operation.

Figure 3:
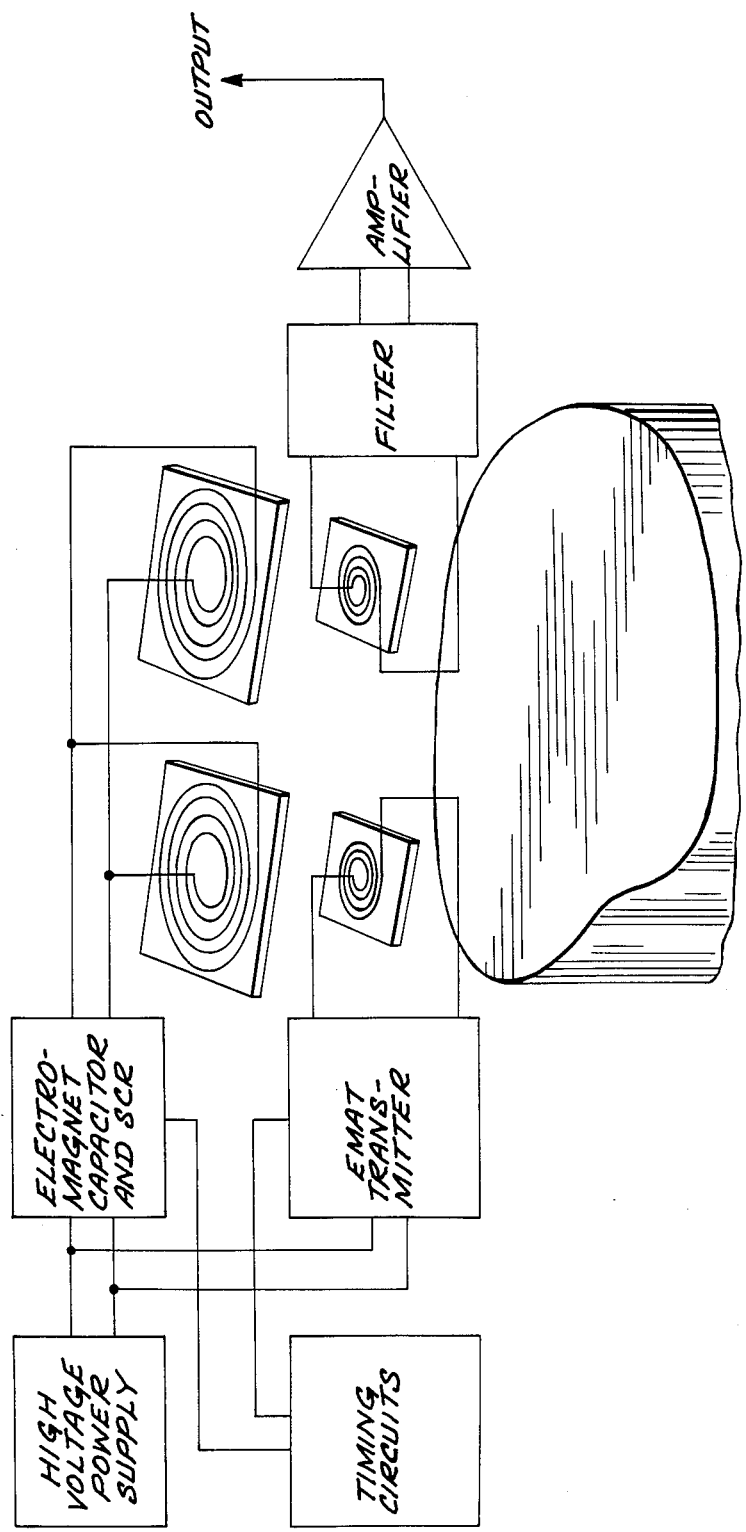
FIG. 3 is a flow chart of the process for using the EMAT.

The EMAT 20 and the EMAT 44 may be used either to excite ultrasonic waves in workpieces, thereby acting as the transmitter, or to receive ultrasonic waves in workpieces, thereby acting as the receiver. The same EMAT can sometimes be used for both purposes, under proper electronic control. The general procedure of operation of the EMAT is illustrated in FIG. 3. A pair of EMATs of the type just described are first provided. An electrical current from a capacitor and SCR is passed through the magnetization coil, to apply a magnetic biasing field to the upper surface of the workpiece. For the EMAT transmitter, a voltage is applied to the eddy current coil from an EMAT transmitter, while the upper surface of the workpiece is magnetized, thereby producing a mechanical acoustic wave in the surface of the workpiece. For the EMAT receiver, the acoustic wave produced by the transmitter must arrive in the area under the receiver while the magnetic field is applied. The small deformation of the near-surface region under the receiver eddy current coil induces a corresponding voltage signal in this eddy current coil, and the voltage can be detected and amplified. The output of the EMAT receiver is first filtered to prevent the low frequency pulse in the magnetization coil from overpowering the high frequency receiver amplifier, and the signal passing the filter is amplified as needed. If the transmitter and receiver functions are sufficiently separated in time and the acoustic wave to be measured is a reflected wave, then a single EMAT can function both as the transmitter and receiver. Otherwise, each EMAT transducer serves as a separate transmitter or receiver.

It is preferred that the current to the magnetization coil be pulsed to high levels, and that the eddy current coil be operated during a quasi-static portion of the pulse. Pulsing the current to the magnetization coil allows higher power levels to be obtained, and restricts the magnetic field to the regions of the workpiece nearest the surface. The principles of the operation of the EMAT are as described in U.S. Pat. No. 4,466,287, whose disclosure is herein incorporated by reference. However, the response of ferromagnetic workpieces to the flat coil EMAT described herein and the iron core electromagnet of the U.S. Pat. No. 4,466,287 is quite different, for the reasons discussed previously.

Figure 4:
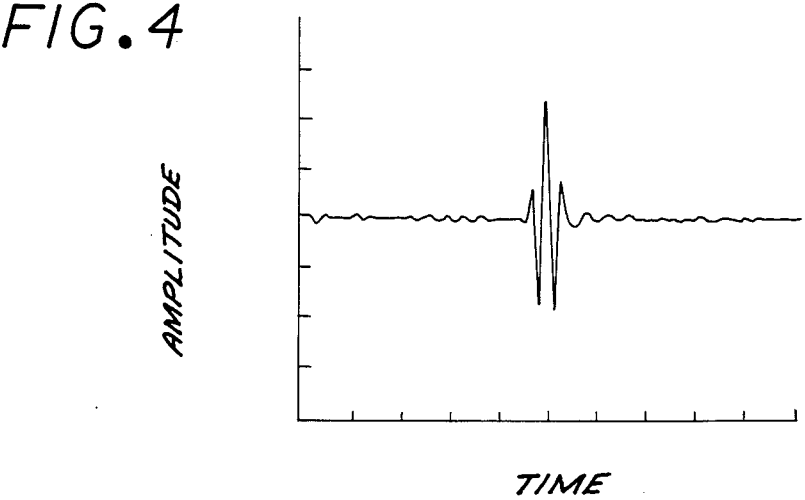
FIG. 4 is a tracing of an oscilloscope display of the ultrasonic waveform produced by a transmitter and receiver pair of EMATs of the invention.

The packaged, high-temperature EMAT 44 has been constructed and used to perform measurements at ambient and elevated temperatures. FIG. 4 shows the output waveform of a single pulse of a transmitter EMAT, as received by a receiver EMAT positioned on the opposite side of a 2 inch piece of aluminum, at ambient temperature. In this case, the transmitter EMAT and the receiver EMAT had magnetization coils powered by different power supplies. The transmitter EMAT had a peak current of 370 amperes with a peak duration of 0.3 microseconds. The receiver had a peak current of 1200 amperes with a peak duration of 300 microseconds.

The following Examples are illustrative of the invention, and should not be taken as limiting the invention in any respect.

EXAMPLE 1

A high temperature EMAT of the type illustrated in FIG. 2 was constructed. The outside diameter of the cylindrical cup 62 in FIG. 2 was about 2.1 inches and the length was 1 inch. The cup was constructed of alumina. The magnetization coil was of the spiral type shown in FIG. 2 fabricated from 20 turns of #18 wire (diameter 0.040 inches). The magnetization coil was cast into an Epoxy plug so as to retain its pancake shape and inserted into the container 50. The container 50 was made of alumina, and had an outside diameter of 1.9 inches so that it would slidably fit within the inner diameter of the cup 62 and be adhesively bonded therein along a cylindrical surface. The thickness of the base 66 of the cup was ground to 0.060 inches in order to minimize the distance between the workpiece and the coils.

Two eddy current coils were used within a single housing 62, one for the transmitter and one for the receiver. Each was wound from 0.006 inch diameter nickel wire with a 0.001 inch thick ceramic coating around them for electrical insulation. These two coils were intermeshed and coplanar, and were wound at the same time using two separate nickel wires carefully held side-by-side while the spiral shape was created. Each coil contained about 30 turns and the pair occupied a circle 1.4 inches in diameter. This pancake shaped array was adhesively bonded to the inside bottom of the cup 62 using a high temperature cement. A stainless steel cap 60 sealed the end of the magnetizing coil container and was held in place and made water tight by an RTV adhesive between the steel and the ceramic. Water was circulated through tubes 58 to keep the magnetizing coil cool and to extract heat from the cup 62.

When assembled, the ceramic end of the structure was slightly more than 1 inch long and 2 inches in diameter, and the water cooling tubes extended about 24 inches from the ceramic. In total, the entire unit weighed about two pounds and could be easily scanned about or held lightly against a hot object using the water tubes as a handle.

When connected to the circuit diagrammed in FIG. 3, ultrasonic signals produced by the transmitter eddy current coil were detected by the receiver eddy current coil when the ultrasonic waves were reflected from the face of a workpiece opposite to the face where the ceramic probe was placed. Samples of aluminum, stainless steel, and ferritic iron were all successfully interrogated with the sound waves generated and detected by this apparatus.

EXAMPLE 2

The EMAT described in Example 1 was used as a combined transmitter and receiver for tests conducted on a 2.8 inch thick aluminum block near its melting point. A pulsed current of about 2300 amperes was passed through the magnetization coil, inducing a magnetic field of about 1.2 Tesla (12 kilogauss) in the near-surface regions of the aluminum workpiece, which was positioned in light contact with the ceramic front face of the probe. The pulsed magnetization current was applied in the form of a half sine wave having a period of about 300 microseconds. With the induced magnetic field at its maximum, an 18 ampere peak-to-peak current tone burst lasting eight cycles of a 3 megahertz frequency signal was applied to the eddy current transmitter coil. A corresponding acoustic wave was thereby induced in the aluminum workpiece, and an ultrasonic echo reflection from the opposite face of the aluminum workpiece was detected by the receiver eddy current coil after a 21.5 microsecond time of flight in the workpiece.

EXAMPLE 3

The two-function transducer of Examples 1 and 2 was used to measure the propagation of sound in the 2.8 inch thick aluminum block at various elevated temperatures. The transducer was rested lightly on the surface of the aluminum piece while the aluminum piece was in a furnace. No liquid or grease couplant was applied, and the probe only touched the surface at a few points. It could be moved easily from point to point on the workpiece surface. This approach provides a vast improvement over the prior approach of attempting to move a bulky, 100 pound electromagnet assembly over the surface of the workpiece.

Figure 5A:
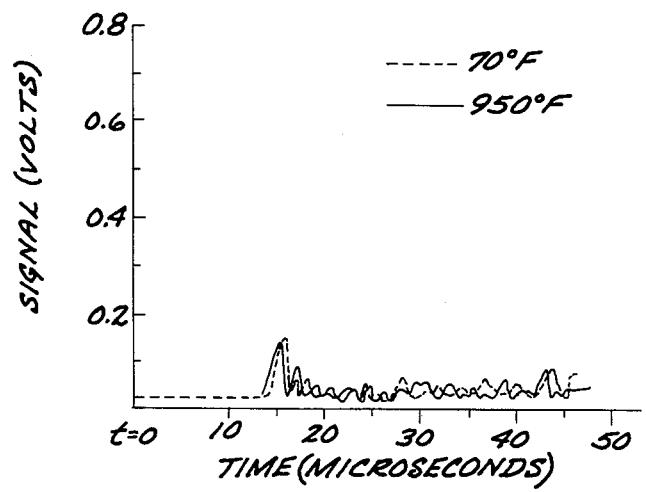
FIGS. 5A and 5B are tracings of oscilloscope displays observed with a high temperature EMAT, for the cases of (A) a gross internal defect in the specimen and (B) no internal defect in the specimen.
Figure 5B:
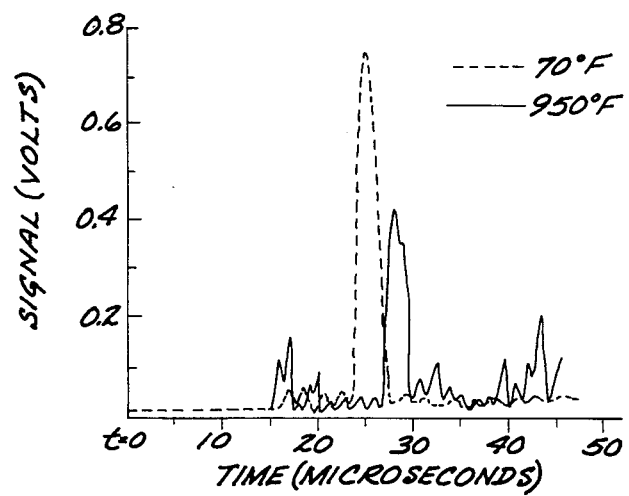

By moving the EMAT probe over the surface and observing the amplitude and arrival time of the ultrasonic wave reflected by the back surface, it was possible to detect flaws on the inside of the block. A flaw, if present, may scatter the ultrasonic wave so that no return signal is received, or an echo signal may appear after an abnormally short transit time. More often, a large flaw prevents the sound wave from reaching the back surface so that the normally observed back surface reflection is absent. FIG. 5 shows two oscilloscope pattern tracings from this work. In FIG. 5A, a large flaw present under the transducer scattered the energy of the ultrasonic wave, and no back wall reflection was seen. By comparison, in FIG. 5B there was no such gross flaw in the path of the ultrasonic wave, and there was a reflection received at about 28 microseconds when the aluminum workpiece was at 950° F. (Due to oscilloscope triggering, the time that the acoustic signal required to traverse the workpiece from the transmitter to the receiver was about 3.5 microseconds less, or about 24.5 microseconds.) At ambient temperature, the reflection was received back at about 25 microseconds, or about a 21.5 microsecond wave propagation time when corrected for the oscilloscope triggering. By comparison with the transit time determined by the study reported in Example 2, this was the back surface reflection.

This type of experiment was repeated over a range of temperatures from 75° F. to 950° F. With increasing temperature, the transit time for the receipt of the back wall signal increases, and the amplitude of the returned signal decreases, as illustrated in FIG. 5B. In order to utilize such data for nondestructive testing, the amplitude and transit time are necessary. The following table lists this information for the testing described, with the reported "Time" being the time required for the wave to propagate, corrected for the oscilloscope triggering delay.

| Temperature °F. | Amplitude volts | Time microsec |
| --- | --- | --- |
| 75 | 3.6 | 21.5 |
| 200 | 3.5 | 21.5 |
| 400 | 3.2 | 21.7 |
| 600 | 2.4 | 22.7 |
| 700 | 1.7 | 23.1 |
| 800 | 0.9 | 23.5 |
| 900 | 0.3 | 24.1 |
| 950 | 0.4 | 24.5 |

EXAMPLE 4

An EMAT receiver transducer for use at very high temperatures was constructed and tested at ambient temperatures. The EMAT receiver was generally similar in configuration to that illustrated in FIG. 2. A ceramic cup 62 approximately 1½ inches in outside diameter and ½ inch long supported the eddy current coil 48, which was a single spiral of nickel wire 0.006 inches in diameter with a 0.001 inch layer of ceramic insulation. This pancake type eddy current coil was permanently attached to the crucible bottom using a high temperature cement. The crucible itself was held in place over the container or heat exchanger 50 by a spring clip so that it could be easily replaced if repairs are needed. The container 50 was a cylinder of thin walled stainless steel approximately 1.5 inches long which was threaded to screw into the heat exchanger cap 56. Inside the stainless steel cylinder, a magnetizing coil made of copper strip ⅛ inch wide and 0.010 inches thick was wound in a spiral as shown at numeral 46 in FIG. 2. Between each turn of the copper tape, an insulating layer of paper was incorporated, and the entire structure was cast into a plug of high temperature epoxy. Since the copper wire leads to the magnetizing coil were mounted permanently inside the insulating feed-throughs in the stainless steel lid of the heat exchanger 56, the magnetizing coil became a permanent part of the heat exchanger lid. The walls and bottom of the heat exchanger were in the form of a cylinder that could be unscrewed from the lid. With this construction technique, the EMAT eddy current cup, the heat exchanger container, and the magnetization coil and lid could be disassembled into three separate parts. This receiver EMAT was successfully tested at ambient temperature on aluminum, stainless steel and iron using a simple EMAT transmitter as the source of the acoustic waves.

EXAMPLE 5

The EMAT transducer of Example 4 was used as a receiver only on hot steel bodies up to and beyond temperatures of 2300° F. For this application, the ultrasonic transducer was a pulsed laser that excited a compressional acoustic impulse on one surface of a stainless steel workpiece by concentrating the energy in its beam onto a small spot for a short time. The EMAT transducer is within the scope of the invention, but the laser transmitter, in itself, is not. The Example demonstrates that the EMAT of the invention can be used with other types of transmitters, and in particular with the laser transmitters that are used for this purpose.

The EMAT transducer was placed on a seven inch thick stainless steel block opposite to the impact point of the laser beam. The EMAT receiver detected acoustic impulse signals delayed from the firing of the laser by the transit time of the longitudinal ultrasonic wave propagating through the solid. In FIG. 6, the lower trace is the current in the magnetizing coil, indicating the time variation of the magnetic field applied to the steel surface. The upper trace is the time dependence of the output signal of the EMAT eddy current coil. At early and late times A and B after triggering the magnetizing coil, noise signals that were not correlated with the laser pulse were always observed. Near the maximum field, and correctly timed with the laser pulse, the acoustic signal indicated in FIG. 6 was always observed.

As is shown in the five Examples, the EMAT transducer of the invention can be used as a transmitter and receiver, and at ambient and elevated temperatures. The magnetic field intensity is as great from the 1-2 inch diameter transducer, which weighs less than 1 pound, as from a conventional EMAT using a magnet assembly weighing over 100 pounds with dimensions approaching 12 inches on a side and with tapered pole pieces to concentrate the magnetic field to a ¼ inch square EMAT. This large conventional EMAT is simply too unwieldy to use in many practical applications. The transducer of the present invention is therefore much more versatile than the conventional EMAT, and can be used in environments not available to the conventional EMAT.

The coil configurations pictured in FIG. 7 further illustrate the versatility of the present invention. In the conventional EMAT that uses a large U-shaped electromagnet, only limited types of acoustic waves may be generated. In the present invention, the configurations of both the magnetization coil and the eddy current coil may be varied, to cooperate in producing particular types of surface and bulk waves in the workpiece.

Figure 7A:
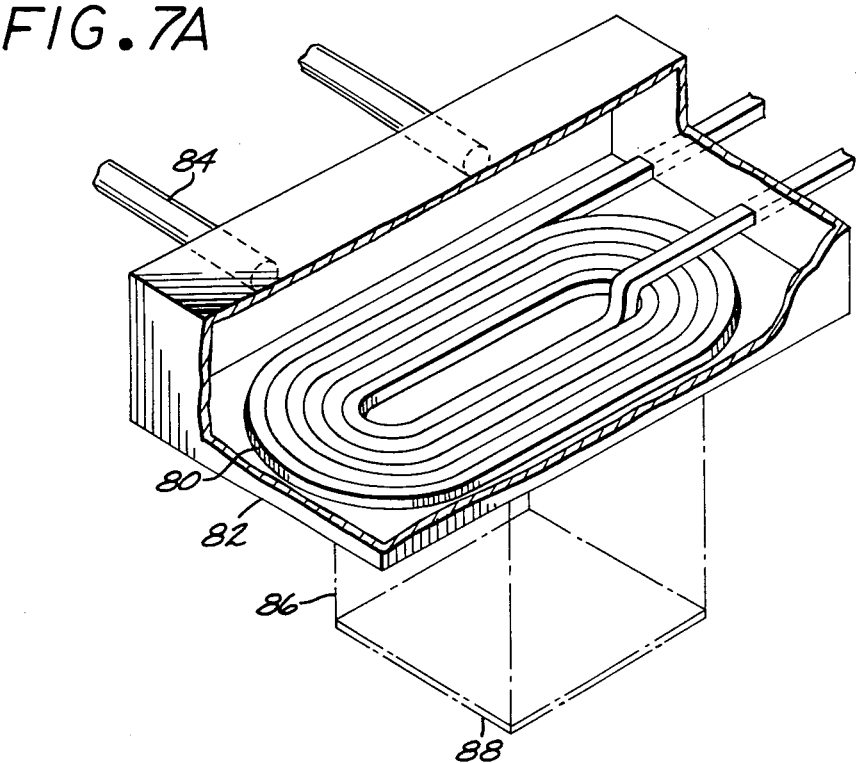
FIGS. 7A–7D are four perspective views of alternative coil configurations, including an elongated spiral magnetization coil and three exemplary eddy current coils.
Figure 7B:
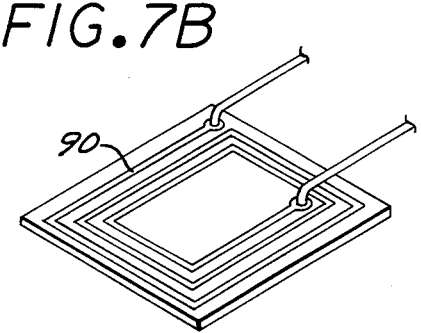
Figure 7C:
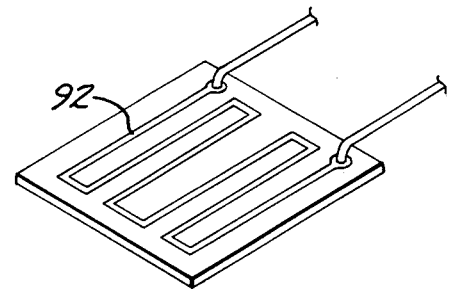
Figure 7D:
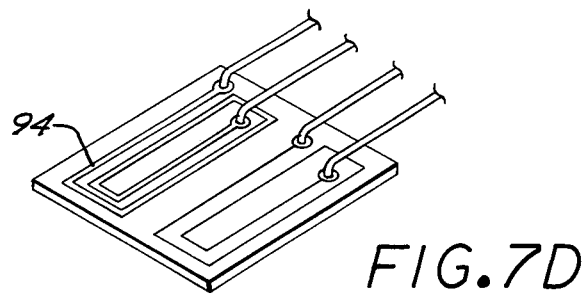

The apparatus of FIG. 7A includes a magnetization coil 80 located within an approriate magnetization coil housing 82. By way of example and not limitation, the illustrated coil 80 is a racetrack configuration. Cooling water is provided, if necessary, to the coil 80 through coolant tubes 84, which circulate coolant through the housing 82. An eddy current housing 86 is attached to the underside of the magnetization coil housing 82. The housing 86 has a base 88, upon which any appropriate eddy current coil can be supported. By way of example but not limitation, FIGS. 7B-7D illustrate three types of eddy current coils that can be supported on the base 88. Operating in conjunction with the magnetization coil, the different types of eddy current coils can produce or detect a range of types of ultrasonic waves in a workpiece below the base 88.

The elongated spiral or racetrack magnetization coil of FIG. 7A produces a pair of areas subject to a uniform tangential magnetic field in a direction parallel to the surface of the workpiece and perpendicular to the long axis of the racetrack. A rectilinear spiral eddy current coil 90 such as shown in FIG. 7B, when placed under the spiral magnetization coil, produces or detects longitudinal waves that propagate essentially perpendicular to the surface of the workpiece. If one side of the spiral eddy current coil is placed under the open hole or slot in the magnetization coil where the magnetic field is essentially perpendicular to the surface of the workpiece, the resulting EMAT produces or detects shear waves.

The meander coil 92 of FIG. 7C produces or detects angle beam waves, Rayleigh waves, or Lamb waves, when used under a spiral or racetrack magnetization coil. By curving the long wires in the meander coil around a common point to the side of the coil, the meander coil produces waves that converge to a focal point inside the material. A pair of linear meander coils 94 such as shown in FIG. 7D can be used with a racetrack magnetization coil to act as separate transmitter and receiver coils in a single unit. Such a configuration is especially useful for generating and detecting angle beam shear wave that propagate between the two coils by way of a reflection from the face of the workpiece opposite to the location of the EMAT coils.

It will now be appreciated that the EMAT of the invention provides an important advance in the art of ultrasonic transducers, permitting non-contact excitation and detection of acoustic waves in workpieces. The device can be packaged to operate under adverse environmental conditions. Although a particular embodiment of the invention has been described in detail for purposes of illustration, various modifications may be made without departing from the spirit and scope of the invention. Accordingly, the invention is not to be limited except as by the appended claims.

What is claimed is:

1. An electromagnetic acoustic transducer, comprising:
   a housing having a base, said housing being constructed of a poorly conducting material;
   a generally planar, electrically conductive magnetization coil, mounted with its plane parallel to said base; and
   a generally planar, electrically conductive electromagnetic eddy current coil with its plane parallel to said base disposed between said magnetization coil and said base, said magnetization coil and said electromagnetic eddy current coil being contained within said housing.

2. The transducer of claim 1, wherein said housing is constructed of a material which is substantially nonconducting.

3. The transducer of claim 1, wherein said housing is cuplike in shape.

4. The transducer of claim 1, wherein said eddy current coil includes at least one meander coil configuration.

5. The transducer of claim 1, wherein said eddy current coil has a spiral configuration.

6. The transducer of claim 1, wherein said eddy current coil has a racetrack configuration.

7. The transducer of claim 1, wherein said magnetization coil has a meander coil configuration.

8. The transducer of claim 1, wherein said magnetization coil has a spiral configuration.

9. The transducer of claim 1, further including a cap on the end of said housing remote from said base.

10. The transducer of claim 1, further including a water cooling jacket within said housing.

11. The transducer of claim 1, wherein the thickness of said base is less than about 0.005 inches.

12. The transducer of claim 1, wherein the distance of said magnetization coil to an outer surface of said base is less than about 0.010 inches.

13. The transducer of claim 1, wherein said housing is made of a material selected from the group consisting of a ceramic, stainless steel, and titanium.

14. An electromagnetic acoustic transducer for testing a workpiece, comprising:

a generally planar, electrically conductive magnetization coil;

a generally planar, electrically conductive eddy current coil; and means for mounting said eddy current coil between said magnetization coil and the workpiece, but without said eddy current coil touching the workpiece.

15. A method for performing acoustic wave testing of a workpiece, comprising the steps of:

furnishing an electromagnetic acoustic transducer, comprising a housing having a base, said housing being constructed of a poorly conducting material, a generally planar, electrically conductive magnetization coil, mounted with its plane parallel to the base, and a generally planar, electrically conductive eddy current coil with its plane parallel to the base, and disposed between the magnetization coil and the base, the magnetization coil and the eddy current coil being contained within the housing;

positioning the base adjacent and parallel to the workpiece to be measured; and measuring the propagation of acoustic waves in the workpiece using the electromagnetic acoustic transducer.

16. The method of claim 15, wherein an acoustic wave is excited in the workpiece by the electromagnetic acoustic transducer, in said step of measuring.

17. The method of claim 15, wherein an acoustic wave is received from the workpiece by the electromagnetic acoustic transducer, in said step of measuring.

* * * * *